United States Patent [19]

Farone et al.

[11] Patent Number: 5,395,419
[45] Date of Patent: * Mar. 7, 1995

[54] THERAPEUTIC AND PREVENTATIVE TREATMENT OF ANAEROBIC PLANT AND SOIL CONDITIONS

[75] Inventors: William A. Farone; Steve Koenigsberg, both of Irvine, Calif.

[73] Assignee: Plant Research Laboratories, Corona del Mar, Calif.

[*] Notice: The portion of the term of this patent subsequent to Nov. 12, 2010 has been disclaimed.

[21] Appl. No.: 4,665

[22] Filed: Jan. 14, 1993

Related U.S. Application Data

[63] Continuation of Ser. No. 718,597, Jun. 21, 1991, abandoned, which is a continuation-in-part of Ser. No. 455,165, Dec. 22, 1989, abandoned.

[51] Int. Cl.$^6$ .................................................. C05G 3/00
[52] U.S. Cl. ........................................... 71/63; 71/11; 71/27; 71/34; 71/64.1; 71/64.11; 71/903; 71/904; 435/262.5; 47/57.6
[58] Field of Search ................ 71/1, 11, 27, 64.10, 71/64.11, 34, 903, 904; 435/262, 262.5; 47/57.6

[56] References Cited

U.S. PATENT DOCUMENTS

| | | | |
|---|---|---|---|
| 2,165,428 | 9/1936 | Waugh | 502/241 |
| 3,796,637 | 3/1974 | Fusey | 502/401 |
| 3,843,517 | 10/1974 | McKinney et al. | 210/611 |
| 3,912,490 | 10/1975 | Boghosian | 71/28 |
| 4,155,738 | 5/1979 | Boghosian | 71/25 |
| 4,171,968 | 10/1979 | Farone | 504/313 |
| 4,293,426 | 10/1981 | Gago | 210/759 |
| 4,326,035 | 4/1982 | Gabellieri | 435/247 |
| 4,399,633 | 8/1983 | Haughey et al. | 47/57.6 |
| 4,410,350 | 10/1983 | Judd | 71/63 |
| 4,414,333 | 11/1983 | Olivieri et al. | 435/243 |
| 4,470,839 | 9/1984 | Gago | 71/34 |
| 4,529,702 | 7/1985 | Bryan | 435/253.6 |
| 4,568,373 | 2/1986 | Yasuhara et al. | 71/6 |
| 4,834,957 | 5/1989 | Van de Walle | 423/268 |
| 5,264,018 | 11/1993 | Koenigsberg et al. | 71/63 |

FOREIGN PATENT DOCUMENTS

| | | |
|---|---|---|
| 0063844 | 11/1982 | European Pat. Off. . |
| 0181210 | 5/1986 | European Pat. Off. . |
| 0181211 | 5/1986 | European Pat. Off. . |
| 3031485 | 8/1980 | Germany . |
| 49-117244 | 8/1974 | Japan . |
| 5333869 | 9/1976 | Japan . |
| 6148495 | 8/1984 | Japan . |
| 9109821 | 11/1991 | WIPO . |

OTHER PUBLICATIONS

Chemistry 7 Industry, No. 18, Sep. 1989, London, GB, pp. 581–584, XP126909 SJEF STAPS "Biorestoration of contaminated soil and Groundwater", see p. 581, left column, line 26–p. 582, right column, line 3.

(List continued on next page.)

*Primary Examiner*—Ferris Lander
*Attorney, Agent, or Firm*—Knobbe Martens Olson & Bear

[57] ABSTRACT

Disclosed is the use of oxygen delivery vehicles, including peroxides of calcium, potassium and magnesium, to treat plant media having a negative reduction oxidation potential. The peroxides are preferably intercalated with phosphate ion which prolongs the period of time during which oxygen is released. The peroxides may be mixed with macronutrients, micronutrients or other beneficial additives or amendments, to provide fertilizers or applied direct to the media. Effective amounts of metals are used as bioactive agents for suppressing or enhancing the activity of microorganisms in the soil, depending on whether such microorganisms are detrimental or beneficial to plants. The formulations are useful in treating anaerobic associated disease states such as black layer in turf. The formulations are also useful in controlling post harvest potato soft rot and other microbial infection and disease states in plants.

20 Claims, 3 Drawing Sheets

OTHER PUBLICATIONS

Z. Yang et al., "System for Simultaneous Study of Bacterial and Plant Geen Expression in Soft Rot of Potato", Molecular Plant–Microbe Interactions, vol. 2, No. 4: 195–201 (1989).

"Mighty Microbes", Chemical Engineering, Mar. 1991, pp. 30–35.

Madsen, et al., "In Situ Biodegradation: Microbiological Patterns in a Contaminated Aquifer" Section of Microbiology, Science Biol. vol. 252 May 10, 1991.

Travis, M. D., et al., "Bioremediation of Petroleum Spills in Arctic and Subarctic Environments" Jul. 1990 (Abstract).

Hinchee, R. E., et al., "Enhanced Bioreclamation o Jet Fuels: A Full-Scale Test at Eglin AFB, Florida" Sep. 1989 (Abstract).

Huling, S. G., et al., "Enhanced Bioremediation Utilizing Peroxide as a Supplemental Source of Oxygen: A Laboratory and Field Study" Feb. 1990.

Tabak H. H., et al., "Laboratory Studies Evaluating the Enhanced Biodegradation of Weathered Crude Oil Components through the Application of Nutrients", Jun. 1990 (Abstract).

Powell, R. M., et al., "Comparison of Methods to Determine Oxygen Demand for Bioremediation of a Fuel Contaminated Aquifer" Sep. 1988 (Abstract).

Britton, L. N., et al., "Aerobic Denitrification as an Innovative Method for in situ Biological remediation of Contaminated SubsurfaceSites", Jan. 1989.

Christiansen, M. L., et al., "Nitrogen Utilization and Digestability of Amino Acids by Lambs Fed a High–Concentrate Diet with Limestone or Magnesium Oxide", J. Anim. Sci. 68(7), 1990. 2095–2104 (Abstract).

Van Ravenswaay, R. O., et al., "Comparison of Methods to Determine Relative Bioavailability of Magnesium in Magnesium Oxides for Ruminants", J. Dairy Sci., 72 (11), 1989. 2968–2980 (Abstract).

Gerba, C. P. et al., "Microbial Removal and Inactivation from Water by Filters Containing Magnesium Peroxide", J. Environ. Scie Health Prt A Environ Sci Eng 23(1) 1988 41–58 (Abstract).

Bourrelly, P., et al., "Freshwater Algae Sampled by F. Starmuelhners Mission in New–Caledonia in 1965 Excluding Diatoms 2,. Chlorophyceae Desmidiaceae and Charophyceae", Rev Hydrobiol Trop 17(2) 1984. 101–116 (Abstract).

Bourrelly, P., et al., "Fresh–Water Algae Collected by F. Starmuhlners Expedition in New–Caledonia in 1965 Excluding Diatoms", Rev Hydrobiol Trop 17(1) 1984. 13–85 (Abstract).

Watlington, Percy M., et al., Interbureau By–Lines, vol. 4, No. 4. Jan. 1968 (Abstract).

THERAPEUTIC AND PREVENTATIVE TREATMENT OF ANAEROBIC PLANT AND SOIL CONDITIONS

This application is a continuation of application Ser. No. 07/718,597, filed Jun. 21, 1991, and now abandoned, which is a continuation-in-part of application Ser. No. 455,165, filed Dec. 22, 1989, now abandoned and entitled "Metallic Peroxides as Supplements for Plants," and of PCT Application No. PCT/US90/07573, filed Dec. 20, 1990, and entitled "Peroxides with Enzyme Active Metals as Supplements for Plants."

BACKGROUND OF THE INVENTION

The present invention relates to the use of certain peroxides, and mixtures of these peroxides with phosphates or surfactants, or both, as agents which release oxygen to the soil. In particular, this invention relates to a method of using certain metal peroxides or metal peroxide/phosphate/surfactant mixtures as a preventative or therapeutic treatment of anaerobic soil conditions, by directly applying the metal peroxide or mixtures thereof to the soil, or blending the metal peroxide or mixtures thereof with plant nutrients, growth regulators or other beneficial additives, and then applying to the soil.

A variety of oxygen delivery vehicles are known in the art. For example, U.S. Pat. No. 3,912,490 to Malcolm B. Boghosian discloses aqueous plant nutrient systems involving the use of urea peroxide or hydrogen peroxide as supplements to fertilizers which release oxygen to the soil. The solution is applied to the soil or other media in which the plant grows. The solution penetrates the soil, releasing oxygen to the root zone. This oxygen treatment is stated to improve plant appearance and prevent injury to the plant due to over watering.

The Boghosian supplement may include nitrogen, phosphorus and potassium in the appropriate ratios and concentrations as required by the particular plant being fertilized. The nitrogen, potassium and phosphorus are macronutrients. The application of nutrients is controlled by the amount in the fertilizer formulation and the rate at which the fertilizer is applied through mixing with water. The Boghosian formulation requires an aqueous system which is limited to relatively low amounts of included macronutrients due to the solution becoming unstable and prematurely releasing hydrogen peroxide which, in turn, releases oxygen. Urea peroxide is a complex of urea and hydrogen peroxide with rather low binding energy. Similarly, the aqueous Boghosian formulation is limited in the use of micronutrients such as trace metals because the micronutrients react with the urea peroxide releasing hydrogen peroxide which, in turn, releases oxygen.

Calcium peroxide has also been used as a supplement for growing potatoes. The calcium is believed to be beneficial for potatoes and oxygen is released to the root zone. Interox Chemicals, Ltd. of Warrington, United Kingdom sells a product Fertilox containing calcium peroxide which is used as a plant supplement.

In addition, U.S. Pat. No. 3,796,637 to Fusey states that the use of compositions of 10 to 40% by weight of iron oxide, manganese dioxide, zinc oxide or an alkali metal peroxide (monovalent series, e.g., sodium peroxide or potassium peroxide from group 1A of the Periodic Table), promotes the biological degradation of hydrocarbon waste material.

Notwithstanding the foregoing, there remains a need for an effective treatment of a variety of disease, toxic, or otherwise undesirable or detrimental states which have been associated with anaerobic and aerobic environments. For example, there remains a need for an effective treatment or preventative method for such conditions as that known in the turf industry as "black layer." In addition, there remains a need for an effective treatment or preventative method for what is referred to in the plant agriculture industry as post harvest "potato soft rot."

SUMMARY OF THE INVENTION

There has been provided in accordance with one aspect of the present invention a method of treating media in which plants grow. This invention is particularly effective in media of the type having a relatively negative reduction-oxidation potential. In accordance with the method, a composition containing peroxide is applied to the media in an amount which releases to the media an effective amount of atomic oxygen to provide an initial increase in the reduction-oxidation potential. Preferably, a composition containing an oxygen release rate mediated peroxide is used. This initial shift of the reduction oxidation potential in the positive direction offsets the negative effects of having a relatively negative reduction oxidation potential, thereby enhancing plant growth and appearance.

Preferably, the peroxide is selected from the group consisting of calcium peroxide, potassium peroxide and magnesium peroxide. The oxygen release rate modifier preferably comprises a compound which provides a source of phosphate ion, such as potassium dihydrogen phosphate, dipotassium hydrogen phosphate, urea phosphate, monoammonium phosphate, diammonium phosphate and mixtures thereof.

The composition preferably also includes a surfactant in an amount which is substantially non-toxic to plants, and preferably is within the range of from about 0.03 to about 1.60 g per gram of peroxide.

In accordance with a specific application of the method of the present invention, there is provided a method of treating black layer in turf comprising the steps of identifying a turf region which exhibits indicia of, or the potential to develop black layer, and administering to the affected turf and effective amount of a composition comprising an oxygen delivery compound selected from the group consisting of calcium peroxide, magnesium peroxide, potassium peroxide and combinations thereof. Preferably, the compound also includes a phosphate ion source and/or a surfactant.

In accordance with a further specific application of the present invention, there is provided a method of treating potato soft rot comprising administering to a harvested potato an effective soft rot treating amount of a composition comprising a compound selected from the group consisting of magnesium peroxide, calcium peroxide, potassium peroxide and mixtures thereof, preferably in combination with an intercalated phosphate source.

In accordance with a further aspect of the present invention, there is provided a method of treating plants or plant portions such as from potatoes, or any other susceptible crop, prior to planting said portions. In accordance with this method, the plant or plant portions are contacted with an effective amount of a composition comprising a compound selected from the group consisting of magnesium peroxide, calcium peroxide, potassium peroxide and mixtures thereof, preferably in combination with an intercalated phosphate source, to inhibit the onset of detrimental conditions of the type which are treatable by said composition.

In accordance with a further aspect of the present invention, there is provided a method of storing plants or plant parts, such as with post-harvest storage prior to use, shipment or prior to planting or any other post-harvest treatment. In accordance with the post-harvest storage method, the plant or plant part is contacted with an effective amount of a compound selected from the group consisting of magnesium peroxide, calcium peroxide, potassium peroxide and mixtures thereof, preferably in combination with an intercalated phosphate source, for inhibiting the onset of detrimental conditions of the type which are treatable by said compound.

Also provided in accordance with the present invention are methods of treating crops having an undesirable condition of the type associated with anaerobic microorganism activity. Also provided is a method of preventing an undesirable crop condition during growing or storage of the crop, the condition being of the type associated with anaerobic microorganism activity. In accordance with these methods, a plant crop having a propensity to develop or already having symptoms of undesirable levels of anaerobic microorganism activity are identified. An effective anaerobic microorganism activity inhibiting or treating amount of a composition comprising a compound selected from the group consisting of calcium peroxide, magnesium peroxide, potassium peroxide and combinations thereof, preferably in combination with an intercalated phosphate source, is administered to the crop to either treat or inhibit the condition.

Further features and advantages of the present invention will become apparent to one of skill in the art based upon the detailed description of preferred embodiments which follows, taken together with the appended claims.

DETAILED DESCRIPTION OF PREFERRED EMBODIMENTS

Figure 1:
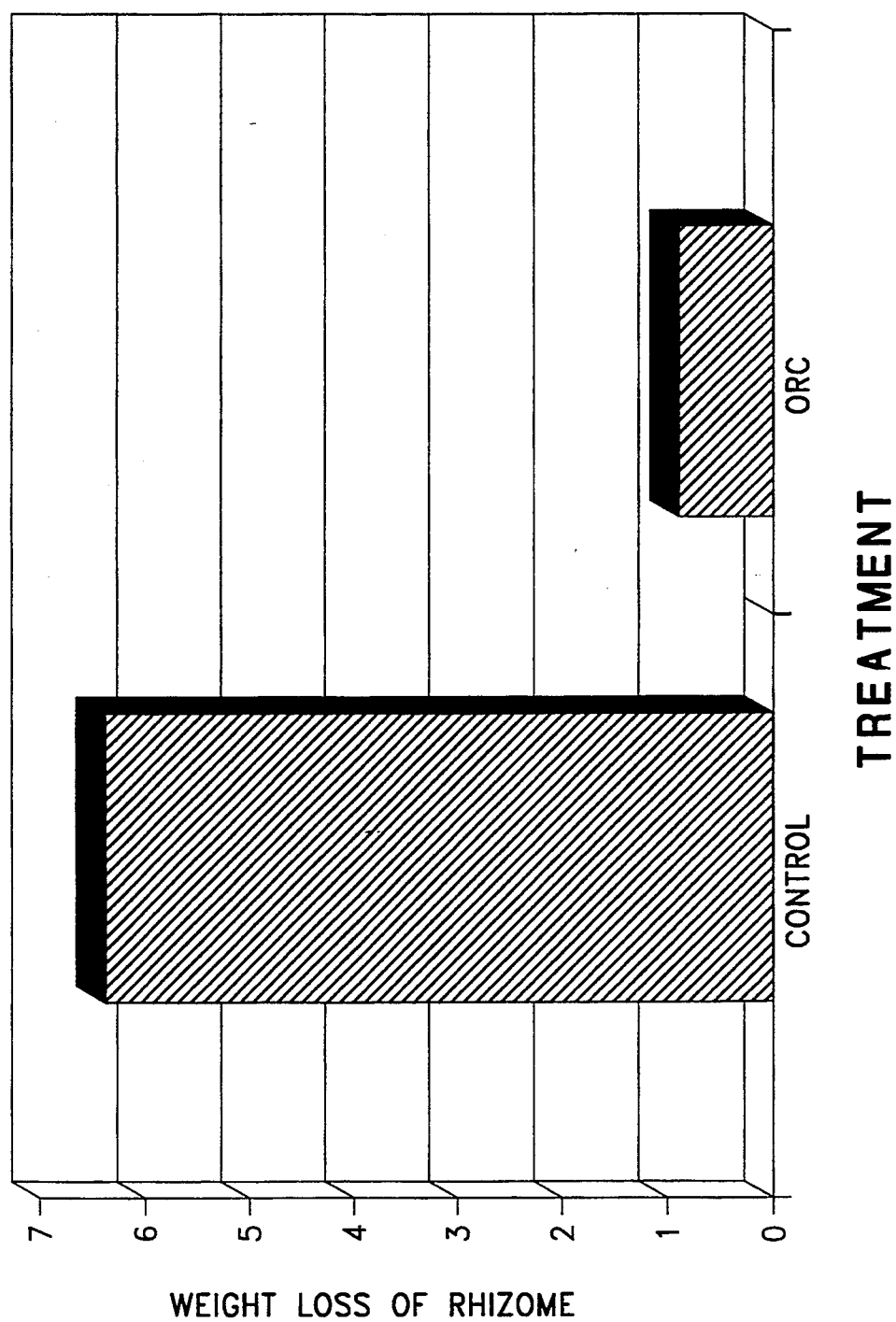
FIG. 1 illustrates the improved storability of calla rhizomes when treated in accordance with the present invention.

The present invention is based upon the discovery that certain formulations, hereinafter described as oxygen releasing compounds (ORCs), have preventative and therapeutic properties in relation to certain disease, toxic, or other detrimental conditions affecting turf and a variety of other plants. Specific ORC compositions useful in practicing the method of the present invention are discussed below. The compositions and methods in accordance with the present invention are useful, but not limited to, the control of black layer in turf grass, post harvest soft rot in potatoes, and as a pre-plant treatment in potatoes.

The basis of the preventative and therapeutic actions of ORC is believed by the inventors herein to involve, inter alia, its ability to release oxygen. Although the complex chemical reactions of the soil environment are beyond complete description, using the current state of the art, the empirical evidence developed by the inventors leads them to conclude that the oxygen release characteristics of the compounds and formulations disclosed herein, have beneficial effects in the control of black layer and harmful microorganisms.

A central parameter in soil chemistry is the reduction-oxidation potential. The so-called "redox" potential is an electrochemical background condition, which controls the chemical reactivity of ions in soil. The present invention is directed to making negative redox potential media "less negative," or slightly positive redox potential media "more positive." Thus, as used herein, references to moving the redox potential from negative to positive refers to the direction of the change, not necessarily a change from absolute negative (below zero) to absolute positive (above zero).

A positive redox potential, referred to as an oxidized environment, is generally beneficial to plant growth. Conversely, unhealthy soils tend to have a negative redox potential, which is detrimental to plant growth. The common terms, sweet and sour soil, relate respectively to the above descriptions and the characteristic smells are a function of the different chemistry in each condition.

Black layer develops under negative redox potentials. Chemically, the condition is characterized by the presence of iron and manganese sulfides (FeS and MnS), which are relatively insoluble dark to black compounds that precipitate and become visually apparent in the soil column. The sulfides are formed and are stable in relatively negative redox environments and may transform to the soluble, lighter colored sulfates ($FeSO_4$ and $MnSO_4$), in relatively positive redox environments.

ORCs, by virtue of their oxygen release capability, tend to provide an initial increase in the redox potential in the positive direction. As sulfides turn into sulfates, the dark to black coloration disappears, the accompanying odor disappears, and iron and manganese become available to the plants.

As an additional benefit of the foregoing solubility changes, the resulting increase in available iron is particularly important in turf management. Furthermore, the phosphates which are present in certain time release ORC formulations in accordance with the present invention, will form complexes with Fe and Mn thereby minimizing the formation or reformation of the respective sulfides.

In addition to providing the basis for the color characteristics of black layer, the sulfides form insoluble precipitates, which in turn have a detrimental effect on the water status of turf by reducing soil porosity. On putting greens in particular, the presence of an impervious black layer zone or zones (hereinafter referred to as zone) can cause a perched water table, which in turn can lead to anoxic conditions in the root zone. Even in drier conditions the black layer zone is toxic and therefore impenetrable to plant roots. Although each of the foregoing conditions has been observed in association with the others, no representation is intended with respect to which conditions may or may not be a cause of any other detrimental condition. The presence of a black layer zone in the soil profile has thus been observed to be particularly restrictive to plant growth and development.

Malodorous conditions, as well as the genesis of the aforementioned toxic nature of the black layer zone, is a function of several genera of anaerobic, sulfur reducing bacteria such as, but not limited to, Desulfovibrio, Desulfotomaculum, Desulfomonas, Desulfonema, and Desulfobacter. These bacteria will convert sulfur to a variety of detrimental sulfur compounds including hydrogen sulfide gas ($H_2S$) which has the characteristic smell of rotten eggs and various mercaptan compounds which also have very disagreeable odors.

These anaerobic bacteria thrive in deoxygenated, relatively negative redox environments. Sulfur becomes the alternative electron acceptor when oxygen is unavailable, but, as an example, if there were adequate oxygen in the soil, $H_2O$ would be formed instead of $H_2S$. By providing oxygen, via ORC, the anaerobic bacteria will either be unable to exist, or in some cases, will produce $H_2O$, thus eliminating some of the noxious compounds associated with black layer.

Although the delivery of oxygen is important to the efficacy of the methods of the present invention, it is also important to note that too rapid a liberation rate, or too high a redox potential, can be detrimental to plant or other desired growth.

The redox potential is a function, not only of the charged species, but also of the concentration of the species and the temperature of the solution. For the case of reactions which involve oxygen in solution, the two important "half reactions" (written as "standard" potentials for unit concentration at 25° C.) are:

acidic solution $$H^+ + \tfrac{1}{2}O_2 + e^- = \tfrac{1}{2}H_2O \quad E_0 = 1.23\ V \qquad [1]$$

basic solution $$\tfrac{1}{2}H_2O + \tfrac{1}{4}O_2 + e^- = OH^- \quad E_0 = 0.401\ V \qquad [2]$$

An overall reaction (which is the sum of "half reactions") proceeds to the right as written if the redox potential is positive. When one uses a redox electrode, one is measuring the tendency for electrons to be lost or gained compared to the electrode. Adding oxygen to the solution will drive the redox value up in either basic or acidic solution because the two reactions above are both positive.

The reactions also depend upon the pH of the media. Again, assuming unit concentration, for example, equation [1] has a voltage given by:

$$E = E_0 - (0.059\ V)(pH) \qquad [3]$$

Thus, with a known pH, [1] can be controlled by the concentration of oxygen and the temperature of the system. If the redox potential is to be changed by adjusting the pH, any of a variety of pH adjusters may be used as will be understood by one of skill in the art, including KOH and $H_2SO_4$. However, it has been determined to be more effective to adjust the redox potential through the use of the ORCs disclosed herein. In addition, pH adjustment can detrimentally affect the desirable microorganisms as will be well known by those of skill in the art.

If the redox potential is too high, everything becomes an electron donor and a variety of damaging reactions can occur. It is therefore desirable to keep the redox potential slightly positive so that the metabolism of the microbes is beneficially changed, but the plants of interest are not harmed.

Slightly higher oxidation potentials than those in [1] and [2] are illustrated below:

$$O_3 + 2H^+ + 2\ e^- = O_2 + H_2O \quad E_0 = 2.07 \qquad [4]$$

$$H_2O_2 + 2\ H^+ + 2\ e^- = 2\ H_2O \quad E_0 = 1.77 \qquad [5]$$

These are somewhat higher than the range which has been empirically observed. As a reference to show that the desired range is in the area of equations [1] and [2], consider that:

$$NO_3^- + 3\ H^+ + 2\ e^- = HNO_2^- + H_2O \quad E_0 = 0.94 \qquad [6]$$

Nitrate is used in plant nutrition as a nitrogen source.

Unfortunately, specific optimal redox potential ranges for use in the present invention cannot be accurately set forth due to the chemical complexity of the in situ or other soil system.

The foregoing does indicate, in a general sense, that $MgO_2$ oxygen reacts roughly as per [1] and [2] and, consequently, it is not in the range, such as with $H_2O_2$ concentrates and $O_3$, where damage to microbes and the plants of interest and other detrimental chemistry can occur. In an alternative view, leading to the same conclusion, we know that $MgO_2$ has a lower redox value than $H_2O_2$, under the same (standard) conditions, because $MgO_2$ is made from $H_2O_2$. Thus, by the laws of thermodynamics, this could not occur if $MgO_2$ could oxidize water to give $H_2O_2$. Concentrated hydrogen peroxide is a stronger oxidizing agent (higher redox potential) and thus is more difficult to control. Thus, one objective of the invention is to beneficially increase the amount of oxygen for the microbes and the plants of interest without unwanted side reactions due to oxidative mechanisms.

Introduction of oxygen into the soil by ORC, whether as a result of the foregoing mechanisms or otherwise, has been determined by the inventors herein to function both as a preventative and as a therapeutic to the development of black layer. There has therefore been provided in accordance with the present invention a preventative or therapeutic treatment for any anaerobic soil conditions, comprising the application of any feasible peroxides, as agents which release oxygen to the soil. The anaerobic soil conditions that merit preventative or therapeutic measures include, but are not limited to, those that generate malodorous or otherwise undesirable conditions. Feasible peroxides are defined as any peroxide which can be used in a soil system, within defined limits, in a safe and effective manner.

Although the redox potential of a given oxygen delivery system (i.e., feasible peroxides) may provide a rough indicator of its efficacy, the suitable oxygen delivery systems are best determined empirically, to determine the actual impact on microbes and the plants of interest. Based upon the disclosure herein, feasible peroxides can be identified by one of skill in the art through routine experimentation. The objective would be to increase the redox potential, preferably to above zero, near about 0.1 volts. Feasible peroxides include, but are not limited to, hydrogen peroxide, urea hydrogen peroxide, sodium percarbonate, calcium peroxide, potassium peroxide and magnesium peroxide. In addition, zinc peroxide may be used in combination with others. Of the divalent Group II A alkaline metals series, e.g., $Be^{++}$, $Mg^{++}$, $Ca^{++}$, $Sr^{++}$, $Ba^{++}$ and $Ra^{++}$, peroxides of $Mg^{++}$ and $Ca^{++}$ are preferred in the context of the present invention.

More specifically, the present invention incorporates certain properly sized metal peroxides and mixtures of these metal peroxides with phosphates or surfactants, or both, as agents which release oxygen to the soil. Furthermore the specific invention is utilized as a preventative and therapeutic treatment, including such agronomic condition(s) as that referred to as black layer, defined as an anaerobic soil condition detrimental to plant growth and development.

By properly sized, it is meant particles having a mesh size of smaller than about 100, but generally no smaller than about 400 mesh. Preferably, mesh size in the range of from about 200 to about 400 will be used.

Particles of less than 400 mesh are relatively unstable and generally unable to deliver oxygen over a sufficient treatment period to effectively carry out the required reactions. In addition, production of excessively small particle size adds to manufacturing costs. However, the smaller particle sizes result in superior particle mobility. Thus, the smallest particle size obtainable, which also exhibits sufficient stability for a given application, is most preferred. Stabilizing relatively small particle size is preferably accomplished in accordance with the "intercalation" method of the present invention, disclosed infra. Alternatively, particle sizes even larger than 100 mesh may be desired to facilitate handling of the product, especially for dry applications.

Although calcium, potassium and magnesium peroxides have all been found useful, these three compounds are not equivalent. Of these three metal peroxides, magnesium peroxide ($MgO_2$) is preferred. It has been determined to exhibit greater stability, simplifying storage and handling. It increases pH only slightly, avoiding making soils too basic, even if a relatively large quantity is employed. It is generally non-toxic in the concentrations contemplated herein (absorption of trace amounts of magnesium is essential in cell biochemistry, in particular, photosynthesis). It delivers the most oxygen per unit weight. Residual magnesium oxide left after release of the oxygen is benign to humans, animals and the environment, and does not appear to create a problem due to overabundance in potted plants.

Although calcium and potassium peroxide are also useful, they do not appear to be as advantageous as magnesium peroxide. The calcium peroxide has a higher basicity than the magnesium peroxide and may therefore be less desirable for use in alkaline soils. It also leaves a chalk residue and tends to bind up micronutrients. Potassium peroxide is corrosive and difficult to handle because it strongly increases pH, it is a strong irritant and releases oxygen very quickly. The calcium peroxide, magnesium peroxide, potassium peroxide or mixtures thereof are preferably present in an amount ranging from about 5 to about 100 and more preferably, from about 5 to about 60 weight percent of the preferred formulation.

The rate at which the metal peroxides will release oxygen to the soil may be inhibited by including an oxygen release rate modifier such as a source of phosphate ion ($PO_4^{-3}$), in the formulation. This is particularly advantageous in applications in which it is desirable to provide the benefits of oxygenation over a time interval which is greater than found with unintercalated metal peroxides. When phosphate is added, to the wet slurry in accordance with the "intercalation" method disclosed herein, it takes a substantially longer period of time for the metal peroxide to decompose to release the oxygen. Preferably, simple phosphate ion (not polyphosphate) will be used. Polyphosphates are less effective per unit weight, less available to plants, and more prone to cause various colloidal effects.

To demonstrate the effect of phosphate intercalation, 11 separate pairs of batches of magnesium peroxide were manufactured by reacting magnesium oxide with hydrogen peroxide. The same methodology was used to make each pair of batches, except that one part had no phosphate ion added while the other part had 3% phosphate ion added during the manufacturing process. The later product is called "phosphate-intercalated, time-release magnesium peroxide." After the reactions were completed, the products were dried.

The active oxygen content of the phosphate-intercalated, time-release magnesium peroxide was higher in all 11 of the pairs of batches than the regular magnesium peroxide. The average percentage increase for the active oxygen content with phosphate intercalation was 22.6%.

These experiments demonstrate that not only does phosphate intercalates of metal peroxide create a controllable time release product as discussed elsewhere in the patent application, but it also increases the yield of the manufacturing process, improves the quality of the product, and lowers the cost of production of the product with a given level of active oxygen. This last point is particularly important, since the major cost component in the metal peroxide manufacturing process is the oxygen source, which is generally concentrated hydrogen peroxide. The phosphate intercalated material is also more stable in terms of shelf life, safety, and handling during field applications.

The amount of phosphate used varies, depending on the desired characteristics sought to be achieved, but generally from about 0.03 to about 1.60 grams of phosphate compound is used per gram of metal peroxide. The molecular structure of the phosphate, and the desired rate of release, control the amount used. Where the release is to be slightly faster, or the phosphate used is desired to be a more acidic buffer (e.g., $KH_2PO_4$), the lower weights are used. Where the release is to take place over longer times, or the soil is acidic and a more basic buffer is desired (e.g., $K_2HPO_4$), the higher weights are used. Thus a slower release requiring an acidic buffer would use a moderate amount of $K_2HPO_4$. These compounds are used in this example since it is easier to see that the percent of $PO_4^{-3}$ is greater in $K_2HPO_4$ than in $KH_2PO_4$.

As a rough approximation, 200 mesh $MgO_2$ in aqueous solution at pH of about 7 (prior to addition of $MgO_2$) at STP will liberate substantially all of the available oxygen within about 100 hours. The intercalation of 0.03 grams of potassium dihydrogen phosphate per gram of 325 mesh $MgO_2$ under the same conditions will extend the oxygen delivery period out to about 14 days. The intercalation of 1.6 grams of potassium dihydrogen phosphate per gram of $MgO_2$ under the same conditions will likely extend the delivery period out to 30 days or even significantly longer depending upon mesh size.

For calcium peroxide, from about 0.03 to about 1.23 grams of phosphate per gram of calcium peroxide is used. For potassium peroxide, from about 0.03 to about 0.80 of phosphate per gram of potassium peroxide is used. For magnesium peroxide, from about 0.3 to about 1.60 grams of phosphate compound per gram of magnesium peroxide is used. The preferred sources of the phosphate ion are potassium dihydrogen phosphate, dipotassium hydrogen phosphate, urea phosphate, monoammonium phosphate and diammonium phosphate.

It is also desirable in some instances to use a surfactant with the metal peroxides. The surfactant has been observed to improve germination of seeds. The surfactant is also desirable because it tends to increase the dispersibility of the metal peroxide in water and in the soil upon application. Typically, from about 0.005 to about 0.020 grams of surfactant is used per gram of metal peroxide. In weight percent terms, the surfactant will generally be present within the range of from about 0.05% to about 2.0% of the ORC composition. Preferably, the surfactant will be present in the range of from about 0.1% to about 1%, and most preferably about 0.1 weight percent of surfactant will be used. For specific applications, however, significantly more surfactant may be desirable.

Surfactants which are generally non-toxic to plants and which have been found useful in germinating seeds, are disclosed, for example, in U.S. Pat. No. 4,171,968, the disclosure of which is hereby incorporated by reference. In general, suitable surfactants include alcohol ethoxylate sulfates, acyl taurides and ethoxylated alcohols. Specifically, the following classes of surfactants are contemplated by the inventors herein:

(1) long chain alcohol ethoxylate sulfates of the formula RO—$(CH_2CH_2O)-_n$ $SO_3Na$ where R is about $C_{12}$ to $C_{18}$, and n is no greater than about 9 to 10;

(2) long chain acyl taurides of the formula $RCON(CH_3)C_2H_4SO_3Na$ where R is about $C_{14}$ to $C_{20}$; and (3) long chain ethoxylated alcohols of the formula RO—$(CH_2CH_2O)-_n$ H where R is about $C_{14}$ to $C_{20}$, and n is no greater than about 9 to 10.

One type of Class 2 surfactants (istheionates) may be obtained from Rhone Poulenc under the trade name Igepon. Other compounds are also suitable surfactants in the context of the present invention. In certain embodiments, the surfactant is a monolaurate, monopalmitate, monostearate and monooleate esters of sorbitol, or mixtures thereof, either with or without ethoxylation. These compounds are sold by ICI America under the brand names of Tween and Span.

For the treatment of black layer and other anaerobic soil conditions which detrimentally affect plant growth, it may also be desirable to include fertilizer nutrients, growth regulators or other beneficial additives in the ORC composition. Fertilizer nutrients will generally not be included, however, in the treatment of some types of conditions such as post harvest control of potato soft rot, but could be incorporated into ORCs which are applied to potato seed pieces as a pre-planting treatment.

The fertilizer nutrients of this invention includes the macronutrients, nitrogen (N), phosphorous (P) and potassium (K). The nitrogen, expressed as atomic nitrogen, is preferably present in the range from about 1 to about 35 weight percent. The phosphorous, expressed as phosphorous pentoxide ($P_2O_5$), is preferably present in the range from about 1 to about 35 weight percent. The potassium, expressed as potassium oxide ($K_2O$), is preferably present in the range from about 1 to about 35 weight percent.

The ratio of nitrogen, phosphorous and potassium may be varied throughout a relatively wide range depending upon the application, as will be appreciated by one of skill in the art.

In accordance with one embodiment of this invention, a fertilizer is provided, including relatively high levels of nitrogen, potassium and phosphorous, and a metal peroxide. For example, fertilizers with an N-K-P value in excess of 15:15:15 are readily achievable in a dry formulation containing metal peroxides. The fertilizer of this invention may also include micronutrients such as trace amounts of iron and manganese, and other ingredients known to be beneficial to plants. Typically, these micronutrients are in amounts ranging from about 0 to about 5 weight percent, preferably 0.1 to 2.0 weight percent. In a preferred fertilizer formulation, the N-P-K ratio is 20:15:15 for general application.

The formulation for use in accordance with the present invention preferably also include small, but effective amounts of certain metals. Suitable metals are selected from the group consisting of zinc, copper, molybdenum, boron, selenium, cobalt, aluminum, manganese, iron, and nickel. Such metals are bioactive agents which either suppress or enhance the growth of selected microorganisms.

An effective amount of metal is sufficiently low that upon application of the composition, to the soil, toxic effects with respect to plants is avoided, and is sufficiently high to affect the microorganisms in the vicinity of the plant roots. The trace elements will generally be in the range of 0.005% to 0.1% for copper; 0.001% to 0.05% for cobalt and nickel; 0.001% to 0.2% for molybdenum; 0.001% to 0.2% for aluminum; 0.01% to 0.4% for zinc; and 0.01% to 0.8% for manganese and iron. In general, an effective amount of metal is less than about 1000 parts per million of the composition (0.1%).

Three general classes of microorganisms are of interest in the context of the present invention: those that are detrimental to plants; those that are beneficial to the plants; and those (natural or genetically engineered) that have been added to the soil to fight other disease organisms or to kill insects. Optimally, formulations in accordance with the present invention will include sufficient quantities of metals to inhibit the first and enhance the second and third of the above classes.

It has been determined that many anaerobic organisms are harmful in the absence of air, i.e., in an anaerobic environment. It also happens that the beneficial organisms (of both class 2 and 3 above) generally require adequate oxygen. Thus, the oxygen releasing properties of the fertilizer formulations of this invention and of the metal peroxides, can also act to optimize all three points above.

Thus, formulations useful in practicing the methods in accordance with the present invention optimally include the following four types of ingredients.

Oxygen releasing metal peroxides are applied to provide oxygen to select the beneficial microorganisms from the pathogenic microorganisms. This is a function in addition to the function discussed above, i.e., providing oxygen to the media or plant tissue. Oxygen release is accomplished in a controlled profile through the use of release rate modifiers to select the beneficial microorganisms over an extended period.

Surfactants are also preferably included to improve suspension of the product in a slurry (as it is essentially insoluble), and to improve dispersion of the composition in the soil during and after application.

Appropriate nutrients can be included in formulations for use in treating black layer and other undesirable conditions which have resulted from or are associated with anaerobic soil conditions. Such nutrients are not only beneficial to the plant but can also help maintain a desirable microorganism population. In accordance with other aspects of the present invention, such as the post harvest control of undesirable conditions such as potato soft rot, plant nutrients may not necessarily be included.

Trace metals at levels which are effective in controlling the enzymatic secretions of the damaging microorganisms are also preferably included. The trace metals can be added in such levels such that the predominant activity is on the microorganisms while the excess, not used in reacting with the microorganism's enzyme systems, can be beneficially used by the plants themselves.

Thus, the compositions of this invention and method of using such compositions can both aid the plants and interact in the desired favorable fashion with microorganisms in the soil that help or hurt the plants.

The aerobic and anaerobic microorganisms present in soil fall into several groupings, including bacteria, fungi and algae. A variety of bacterial diseases of interest to commercial growers include the following: *Cornebacterium insidiosum* causes alfalfa wilt; *Xanthomonas malyagearum* causes leaf spot in cotton; *Xanthomonas stewartii* causes wilt in corn; *Erwinia thacheipilia* causes wilt in cucurbits; *Xanthomonas phaseoli* causes blight of beans; *Xanthomonas campestris* causes black rot of crucifers; *Erwinia amyloyora* causes fire blight in some fruits; *Streptomyces scabies* causes potato scab; *Cornebacterium sepedonicum* causes ring rot in potato; *Erwinia carotovora* causes soft rot in cabbage, lettuce, potato (and other root crops); and *Pseudomonas malkyacearum* causes wilt in cotton.

It has been found that metal peroxides, as evidenced by experimentation with magnesium peroxide, which released at least about 140 mg of oxygen per gram of total formulated product, controls *Erwinia carotovora*. This result can be extended to other species, because the mechanism of action of the bacteria, requires the lack of oxygen to begin the induction of the biochemicals that cause the damage. The addition of the other ingredients will enhance the effect either by benefitting the plant directly, inhibiting the detrimental microorganisms, or by enhancing the soil for the beneficial organisms to have a selective advantage.

In separate tests, the zinc ion in the range of from about 1 to about 10 ppm, in the presence of oxygen and surfactant, was found by the inventors to be effective against damage caused by Cornebacterium species. It is hypothesized that the zinc interferes with enzyme systems used in the attack. Similar effects were found with Pseudomonas species.

This situation continues for the fungi. For example, Taphrina spp. causes leaf curl in peach, pear, oak, etc.; *Glomerella cingulata* causes bitter rot in apple, pear, grape; Nectria spp. and Erysiphe spp. causes mildew; Pythium spp. causes damping off and root rot; Rhizopus spp. and Tilletia spp. cause smut in oats, wheat, rye, barley, sorghum and corn; and Fusarium and Verticillium spp. cause wilt in many plants.

Mildew, damping off and root rot have been controlled in experiments with sensitive seedlings. A combination of the surfactants with the oxygen-releasing peroxides provided evidence of earlier and higher frequency of germination of seedlings with no evidence of these fungal diseases in geraniums, impatiens, and other bedding plants.

In addition, formulations containing copper in the range of 0.1-5 ppm have been found to be useful for control of many of the fungi, particularly Taphrina, Pythium, Tilletia, Ustiago and Fusarium. Copper salts are preferably included in the formulation in an amount so that when applied dry to the soil and then watered, or when the formulation is diluted with water before application, from about 0.1 to about 5 ppm of copper is delivered.

Certain unwanted algae are also sensitive to high levels of oxygen. It has been demonstrated by the inventors herein that ORC, in accordance with the present invention, exhibits both preventative and therapeutic effects. Turf grass was grown within $4''$ dia. $\times 3''$ deep pots (approx. 600 cc soil) in the greenhouse, for the purpose of proving ORC alleviated flooding stress (anaerobic stress) which it did. An unexpected result was control of algae. A minimum 100 mg of ORC (20% activity) was added per pot every two days. This minimum dosage in the experiment demonstrated preventative results. This work was repeated using pots in the greenhouse with algae already growing. The addition of 100 mg/pot twice per week controlled algae, demonstrating therapeutic action as well. In these experiments, 20 mg $O_2$ was added each treatment to a soil volume of about 600 cc. Thus, since soil has a bulk density of about 1.25 g/cc, each $O_2$ dosage was approximately 26 ppm.

In another study, a slurry consisting of 10 g/l was sprayed on a log surface in a nursery. It effectively controlled the algae. It is expected that certain of these algae will also be controlled in accordance with the methods of the present invention.

These applications are important since as much as about 10% of the commercial crops in the United States are lost to disease. In addition, even more would be lost if the use of pesticides is reduced below current levels. Because of this loss, as well as an additional like loss to insects, microbial control of insects and diseases has been gaining recognition as a means of protecting crops. Also, alternative, more environmentally benign treatments such as those of the present invention are becoming more important. An introduction to this field is given by J. W. Deacon in the book, *Microbial Control of Plant Pests and Diseases*, published by the American Society for Microbiology, Washington, D.C., 1983.

In this methodology, beneficial bacteria such as *Bacillus thuringiensis* or *Bacillus popilliae* are added to the soil. Various insect-pathogenic fungi are also in use such as Entomophthora spp., *Beauveria bassiana*, *Metarhizium anisopliae* and *Hirsutella thompsonii*.

These organisms are expected to benefit from an adequate supply of oxygen, as well as the trace metals, macronutrients or other beneficial additives that can be provided by the ORC formulations of the present invention. In the case of these microorganisms, molybdenum, iron, cobalt and nickel are particularly useful in assisting the enzymatic functions that will attack the insect or specific disease organism.

In a similar manner, the natural fungi associated with plant roots, the so-called mycorrhizal fungi, will benefit from the oxygen, trace metals, macro nutrients and other beneficial additives supplied by the ORC formulations of the present invention in aqueous carrier assisted to the soil area by the surfactant. These organisms include, but are not limited to, members of the species Pisolithus, Boletus, Cenococum and Thelephora.

It is difficult to state the specific application rates of the various materials, as will be understood by those of skill in the art, since there is a level in the formulation which, when diluted with water, provides an effective level in the aqueous phase. Factors such as the quality of the water (water hardness, pH, chemical impurities particularly in recycled water), the temperature of the water, the ambient temperature, the soil temperature and the relative humidity will all effect the specific delivery of the beneficial compounds. One should also be aware that certain materials such as Zn, Cu, Mn and other trace metals accumulate in the tissues of either the plants or microorganisms due to the biochemical reactions involved.

A wide variety of different formulations of fertilizers may be made utilizing the principles of this invention. The nominal percentages of the various macronutrients, micronutrients, other beneficial additives and surfactant could be varied to provide fertilizers having formulations tailored to the specific plants and environments in which they are used. The ingredients of these formulations and typical weight ranges are as follows:

| Ingredient | Weight Percent |
| --- | --- |
| magnesium peroxide | 5–60 |
| potassium dihydrogen phosphate | 0–40 |
| dipotassium hydrogen phosphate | 0–40 |
| diammonium phosphate | 0–45 |
| potassium nitrate | 0–40 |
| ammonium nitrate | 0–50 |
| urea | 0–60 |
| trace metals | 0.0–5.0 |
| surfactants | 0.0–0.2 |

The preferred fertilizers of this invention have the following compositions:

Fertilizer I:

from 10 to 25 weight percent magnesium peroxide,
from 10 to 25 weight percent potassium dihydrogen phosphate,
from 15 to 25 weight percent dipotassium hydrogen phosphate,
from 40 to 60 weight percent urea,
from 0 to 2.0 weight percent trace metals, and
from 0 to 0.2 weight percent surfactant.

Fertilizer II:

from 10 to 25 weight percent magnesium peroxide,
from 30 to 50 weight percent diammonium phosphate,
from 15 to 30 weight percent potassium nitrate,
from 15 to 25 weight percent urea,
from 0 to 2.0 weight percent trace metals, and
from 0 to 0.2 weight percent surfactant.

Fertilizer III:

from 10 to 25 weight percent magnesium peroxide,
from 30 to 45 weight percent diammonium phosphate,
from 5 to 30 weight percent potassium nitrate,
from 15 to 50 weight percent ammonium nitrate,
from 0 to 2.0 weight percent trace metals, and
from 0 to 0.2 weight percent surfactant.

Typical formulations are as follows:

| Formulation A | |
| --- | --- |
| 19.96% | magnesium peroxide |
| 15.30% | potassium dihydrogen phosphate |
| 17.96% | dipotassium hydrogen phosphate |
| 46.57% | urea |
| 0.1% | trace metals |
| 0.1% | surfactant |

The above Formulation A is based upon employing chemical quality ingredients and the nominal percentages may vary slightly as a consequence. The magnesium peroxide could be as low as 5 percent in the above formulation and still provide adequate oxygen release. In fertilizers, where a very high oxygen release is required, such as severely flooded soils, the above formulation may contain as much as 50 percent magnesium peroxide. The above Formulation A gives an N-P-K value of 21.74-15.30-15.01, with the P expressed as $P_2O_5$ and K expressed as $K_2O$.

The potassium dihydrogen phosphate appears to be slightly preferred when it is desired that the product release oxygen over a one to two week period. Thus, it may be desirable to employ only this phosphate and not a mixture of the potassium dihydrogen phosphate and the dipotassium hydrogen phosphate. Either or both of these phosphates are added during the preparation of the magnesium peroxide.

If the magnesium peroxide is made by reacting magnesium oxide with aqueous hydrogen peroxide as illustrated in Example 1, Formulation A has been shown to release 48 milligrams of oxygen per gram of fertilizer material blended with a gallon of water. However, even if the magnesium peroxide was in an impure state, for example, only 15 percent of the weight of oxygen in the reaction mix, such a material when used in Formulation A would still provide oxygen release of 30 milligrams of oxygen per gram of fertilizer. Thus, if there is an incomplete reaction during the manufacture of the magnesium peroxide, over-drying, or too long of a delay in drying, the fertilizer product will still have the desired oxygen release property.

Formulation B

It has been found that the magnesium peroxide concentration could be as low as about 11 percent if the magnesium peroxide contains 25 weight percent active oxygen and the oxygen release would still be at least about 29 milligrams atomic oxygen per gram of fertilizer (11.74%×25% activity=29.4). The following Formulation B illustrates such a product.

| | |
| --- | --- |
| 11.74% | $MgO_2$ |
| 18.34% | $KH_2PO_4$ |
| 18.34% | $K_2HPO_4$ |
| 51.36% | urea |
| 0.11% | trace metals |
| 0.11% | surfactant |

Formulation B has a N-P-K value of 23.98:17.04:16.27.

Formulation C

Formulation C provides magnesium peroxide at an active oxygen concentration of 15 percent, and has about 30 mg of atomic oxygen per gram of fertilizer.

| | |
| --- | --- |
| 19.96% | magnesium peroxide |

| | |
|---|---|
| 38.26% | diammonium phosphate |
| 21.62% | potassium nitrate |
| 19.96% | urea |
| 0.1% | trace metals |
| 0.1% | surfactant |

Formulation C is a less expensive fertilizer. Again the diammonium phosphate is added to the magnesium peroxide prior to drying. Diammonium phosphate is slightly hygroscopic and needs to be protected from pickup of moisture. Mixing the magnesium peroxide and the diammonium phosphate before drying is effective in preventing hygroscopic behavior. Formulation C nominally has an N-P-K value of 20.43:20.56:20.15.

Formulation D

Formulation D is based upon the magnesium oxide being present at least 25 percent active oxygen purity. The amount of peroxide may be reduced to provide 29 mg of oxygen per gram of fertilizer. Formulation D is:

| | |
|---|---|
| 11.74% | magnesium peroxide |
| 42.19% | diammonium phosphate |
| 23.84% | potassium nitrate |
| 22.01% | urea |
| 0.1% | trace metals |
| 0.1% | surfactant |

The N-P-K value for this Formulation D is 22.53:22.67:22.22.

Formulation E

In Formulation E, the active oxygen is as low as 15%, and the oxygen release is about 30 mg oxygen per gram of fertilizer:

| | |
|---|---|
| 19.96% | magnesium peroxide |
| 38.26% | diammonium phosphate |
| 21.62% | potassium nitrate |
| 19.96% | ammonium nitrate |
| 0.1% | trace metals |
| 0.1% | surfactant |

The N-P-K value for this Formulation E is 18.11:20.56:20.15.

Formulation F

In Formulation F, the active oxygen is greater than 25%, and the oxygen release is 29 mg/g of fertilizer:

| | |
|---|---|
| 11.74% | magnesium peroxide |
| 42.19% | diammonium phosphate |
| 23.84% | potassium nitrate |
| 22.01% | ammonium nitrate |
| 0.11% | trace metals |
| 0.11% | surfactant |

The N-P-K value for this Formulation F is 19.97:22.67:22.22.

Formulation G

In Formulation G, the active oxygen is at least 15%, and the oxygen release is about 27 mg/g of fertilizer:

| | |
|---|---|
| 17.96% | magnesium peroxide |
| 33.27% | potassium dihydrogen phosphate |
| 6.65% | potassium nitrate |
| 41.92% | ammonium nitrate |
| 0.1% | trace metals |
| 0.1% | surfactant |

The N-P-K value for this Formulation G is 15.61:17.35:17.71.

Formulation H

In Formulation H, the active oxygen is at least 25%, and the oxygen release is about 29 mg/g of fertilizer:

| | |
|---|---|
| 11.49% | magnesium peroxide |
| 35.89% | potassium dihydrogen phosphate |
| 7.18% | potassium nitrate |
| 45.23% | ammonium nitrate |
| 0.11% | trace metals |
| 0.11% | surfactant |

The N-P-K value for this Formulation H is 16.84:18.72:19.11.

In accordance with the method of making the fertilizer enhanced ORC, in accordance with the present invention, the metal peroxide is first prepared in an aqueous solution. In general, the metal oxide, metal hydroxide or metal carbonate, or combination thereof, is reacted with hydrogen peroxide to produce the metal peroxide. The reactions are generally non-stoichiometric. For example, magnesium peroxide could be prepared by one of the following three reactions:

$$MgO + H_2O_2 == MgO_2 + H_2O \quad [7]$$

$$Mg(OH)_2 + H_2O_2 == MgO_2 + 2H_2O \quad [8]$$

$$MgCO_3 + H_2O_2 == MgO_2 + H_2O + CO_2 \quad [9]$$

where
$MgO_2$ is magnesium peroxide
$H_2O_2$ is hydrogen peroxide
MgO is magnesium oxide, also called magnesia
$H_2O$ is water
$Mg(OH)_2$ is magnesium hydroxide
$MgCO_3$ is magnesium carbonate
$CO_2$ is carbon dioxide gas The magnesium oxide and hydrogen peroxide reaction is the preferred way to produce the magnesium peroxide utilized in this invention, from the viewpoint of providing highest oxygen activity. The magnesium carbonate could be used as the starting material and it does not require cooling, but it is more costly. Any suitable source of magnesium oxide, commercial grade, is acceptable, preferably 100 to 400 mesh particles are used if the magnesium peroxide is to be dispersed in water. Particle size is not as important if the magnesium peroxide is to be applied in a dry form. Due to surface area reactivity characteristics, finer particle sizes result in higher activity in the final product.

The hydrogen peroxide is sold as a water solution containing from about 3 to 70 percent by weight of hydrogen peroxide. Typically, the commercial grade solution of hydrogen peroxide contains 30 to 35 percent of the hydrogen peroxide and this is the material typically utilized in the method of this invention.

The reaction of magnesium oxide and hydrogen peroxide is exothermic, and the temperature must be controlled so that excess heating does not occur. Moreover, water is removed after the reaction is completed to produce a dry product. The drying must be done in a manner which does not destroy the metal peroxide which, for example in the case of magnesium peroxide, decomposes at 160° C. or 320° F.

In general, the heating process is preferably controlled so that the temperature does not exceed about 110° C. Temperature as low as 40° C. with vacuum may also be used. The magnesium peroxide does not decompose in any significant quantities under such temperature conditions. It is important that the magnesium peroxide formed be maintained as a peroxide, so that the desired oxygen release characteristic is attained when applied to soil. The best way to make magnesium peroxide with the highest oxygen activity, presently known to the inventors, is to vacuum dry at the lowest possible temperature.

It is desirable during the production of the metal peroxide that the maximum amount of metal peroxide be produced. For example, magnesium peroxide, if perfectly pure, would contain 28.4 percent by weight oxygen for release. For calcium peroxide, the percent by weight oxygen is 22.2 percent. And for potassium peroxide, the percent by weight oxygen is 14.5 percent. Consequently, on a weight-for-weight basis, none of the other metal peroxides match magnesium peroxide. Moreover, at equal levels of active oxygen, the magnesium peroxide will always have the lowest weight in the formulation.

Used with the same concentrations, products using the potassium and calcium peroxide will not deliver as much active oxygen as products using the magnesium peroxide, since they cannot carry as much oxygen per unit weight. The metal peroxide does not, however, have to be perfectly pure. In accordance with this invention, the magnesium oxide is mixed with an aqueous solution of hydrogen peroxide to produce a metal peroxide having an acceptable purity so that it contains at least about 5% and preferably at least about 15% by weight oxygen to be released to the soil.

Since the reaction between the magnesium oxide and hydrogen peroxide is exothermic, the temperature of the reaction must be controlled. This may be accomplished by blending the hydrogen peroxide with the magnesium oxide in two steps. The aqueous hydrogen peroxide solution for a given batch is divided approximately into equal portions. The magnesium oxide is slowly added to one of these portions, allowing the heat to dissipate slowly to avoid explosive or extremely ebullient reaction conditions occurring in the reaction vessel, which is preferably a water-cooled, jacketed container.

Magnesium oxide powder is added to the first portion, preferably in portions or metered at a rate to maintain the temperature of the reacting mixture at about 40° C., with vacuum. After all the magnesium oxide is added, the temperature of the reaction mixture is lowered to about 35° C. and then the balance of the aqueous hydrogen peroxide solution is slowly added with stirring and cooling to avoid an excessively high reaction temperature. This aqueous slurry of magnesium peroxide, which consists of fine particles dispersed throughout the water, is then dried to produce a granular material. This can be accomplished by heating under vacuum, oven drying or spray drying.

It is desirable to control or regulate the rate at which oxygen is released so that the release occurs over a prolonged period of time. To accomplish this, a phosphate-intercalated material such as has been previously described is added to the aqueous medium before completion of drying. The phosphate-containing material, in addition to regulating the rate at which oxygen is released, also provides the macronutrient phosphorous. The dried product containing the magnesium peroxide is then dry-blended with any other desired ingredients, for example urea, which provides the nitrogen and ingredients containing potassium and other supplements such as trace minerals. When it is desirable to include the surfactant, the surfactant is added to the aqueous medium prior to drying, if the surfactant is stable in water. If the surfactant is unstable in water, such as the istheionates, it may be dry blended after drying.

EXAMPLES

The following presents several formulations of the ORC compositions of this invention and the method of making and using these compositions.

EXAMPLE 1

PREPARATION OF MAGNESIUM PEROXIDE

To produce 56.3 grams of magnesium peroxide, 40.3 grams of magnesium oxide and 94 cubic centimeters of a 34 weight percent aqueous hydrogen peroxide solution are used. To ensure completeness of the reaction between the magnesium oxide and hydrogen peroxide, excess hydrogen peroxide, for example, approximately 150 cubic centimeters of the aqueous hydrogen peroxide is acceptable. This is divided into approximately two equal portions. The first portion, or 75 cubic centimeters, is placed in a water-jacketed reaction vessel and the powdered magnesium oxide is added slowly, keeping the temperature of the reaction ingredients at approximately 40° C. After all the magnesium oxide powder has been added to the reaction mixture, the temperature is lowered to 35° C. and the second half of the hydrogen peroxide solution is added to the reaction vessel, with stirring and cooling to prevent the liquid reaction slurry from bubbling out of the reaction vessel. The liquid slurry produced is then dried by heating at a temperature of 90°-110° C. in an oven provided with vacuum to produce a fine granular powdery magnesium peroxide having a mesh size of approximately 325. It is preferable that the magnesium peroxide be in a highly powdered form so that if it is subsequently mixed with water, it can be easily dispersed in the water, since neither magnesium peroxide nor the resulting magnesium oxide produced after release of oxygen is soluble in water.

EXAMPLE 2

TIME RELEASE ORC

This example is similar to Example 1 in that essentially the same amounts of reagents are used. In this example, 43.2 grams of potassium dihydrogen phosphate is dry blended with the magnesium oxide prior to mixing with the hydrogen peroxide solution. The drying is conducted at 40° C. under vacuum. A product with a higher oxygen activity is produced using the procedure of this example than produced in Example 1.

EXAMPLE 3
TIME RELEASE ORC

This example is essentially the same as Example 1, except the potassium dihydrogen phosphate is added to the liquid slurry prior to drying.

EXAMPLE 4
NUTRIENT SUPPLEMENTED TIME RELEASE ORC

This example is similar to that of Example 1 except an entire fertilizer formulation is formed in the aqueous blend. In this example, 40.3 grams of magnesium oxide are added with 43.2 grams of potassium dihydrogen phosphate, 50.7 grams of dipotassium hydrogen phosphate, 131.5 grams of urea, 0.3 grams of trace metals, and 0.3 grams of surfactant. In this example 200 cubic centimeters of hydrogen peroxide solution is used to keep the slurry fluid. The blend is dried at 80°-100° C. under vacuum.

EXAMPLE 5
PEROXIDE/PHOSPHATE/SURFACTANT

This example is essentially the same as Example 2, except 0.3 gram of the surfactant monolaurate sorbitol ester is added to the aqueous slurry of the magnesium peroxide and the potassium dihydrogen phosphate before drying, or following drying in accordance with milling techniques, known in the art.

EXAMPLE 6
PEROXIDE/SURFACTANT

This example is essentially the same as Example 1, except 0.3 gram of the surfactant is added to the aqueous slurry of magnesium peroxide. Upon drying, a powder is provided having a mesh size of 325. This powder may be dispersed readily in water and applied either directly to the soil or used as a seed treatment prior to planting.

EXAMPLE 7
PREPARATION OF CALCIUM PEROXIDE ORC

To prepare 50 grams of calcium peroxide, 38.9 grams of calcium oxide and 38.3 grams of potassium dihydrogen phosphate is added to 54 milliliters of 34% hydrogen peroxide solution slowly to allow thorough reaction. After the mixing is complete another aliquot of 54 milliliters of the hydrogen peroxide solution is added slowly allowing the reaction to go to completion. To the aqueous slurry is added 0.3 gram of surfactant and the slurry is dried at 40° C. in a vacuum.

The dried material containing the phosphate stabilized calcium peroxide is optimally then dried blended with 116.6 grams of urea, 45 grams of dipotassium hydrogen phosphate to provide a fertilizer with an N-P-K of 20:15:15.

EXAMPLE 8
PREPARATION OF POTASSIUM PEROXIDE ORC

To prepare 50 grams of potassium peroxide, 62.7 grams of potassium carbonate mixed with 38.3 grams of potassium dihydrogen phosphate and 0.3 gram of surfactant is added slowly to 70 milliliters of 34% hydrogen peroxide solution. The reaction is carried out inside a vacuum oven so that immediately after the reaction is completed the mixture is dried at 40° C. or less under high vacuum.

The dry reaction product may thereafter be dry blended with 116.6 grams of urea and 45 grams of dipotassium hydrogen phosphate to provide a fertilizer of N-P-K of 20:15:32.

EXAMPLE 9
OXYGEN RELEASE CHARACTERISTICS

The fertilizer formulations A-H disclosed above were tested for oxygen release. When mixed with water, Formulation A and B provide more oxygen and for longer periods of time than the Boghosian product. When phosphate was added to ORC by intercalation, the rate of release of oxygen was slower and extended for longer periods of time, than when the phosphate was absent. Fertilizers of this invention have been used with a wide variety of plants and demonstrated to be effective fertilizers. In comparison testing with other products, the fertilizers of this invention produced better or comparable results even when used at significantly lower dosage levels.

Examples 10-13 which follow demonstrate the therapeutic and preventative effects of the method of the present invention with respect to the treatment of black layer. In each of these examples, ORC is defined as 0-1 or 3-1. This defines the percentages of phosphate (as, but not restricted to, $KH_2PO_4$ and surfactant (as, but not restricted to, Na istheionate), respectively. Therefore, 0-1 is pure $MgO_2$ of a given activity with 0% phosphate and 1% surfactant, while 3-1 is pure $MgO_2$ of a given activity with 3% phosphate and 1% surfactant. A 0-0 formulation would be essentially pure metal peroxide, such as the unamended product of Example 1.

Typically, 10 lbs. of 0-1 or 3-10RC is mixed in 50 gal. of water for a concentration of 0.2 lbs./gal. One then sets the application rate per 1,000 sq. ft. As an example, 2.5 gal. per 1,000 sq. ft. delivers 0.5 lbs. per 1,000 sq. ft. The number of passes then determines the final concentration applied. In the tests involving 1, 2 and 4 lbs. per 1,000 sq. ft., 2, 4 and 8 passes are made with the spray boom assuming the above delivery rate.

The amount of water being applied is somewhat negligible relative to the area to which it is applied and the slurry dries quickly to a powder. Every time the area is watered, the ORC can release oxygen until it is spent. A full irrigation followed each application, to activate the product in a timely fashion, which constitutes a product use recommendation. This is of particular importance if the product is used in conjunction with core aeration techniques. It has been determined that the efficacy of the ORC is maximized if applied following a core aeration treatment, or presumably also following any other method that allows greater physical penetration of the ORC.

EXAMPLE 10
THERAPEUTIC EFFECT ON BLACK LAYER

A series of greens having Bentgrass overseeded with Bermuda grass variety turf at a golf course in Florida, were diagnosed as affected by black layer. Diagnosis was accomplished by visual observation from above the ground, which revealed signs of anaerobic stress. Upon core sampling of the visibly affected area, a characteristic black layer symptomology was observed, including a marked, single or multiple color zonation and odor.

A series of sections of the affected turf were utilized, to demonstrate the efficacy and dose dependency relationship, in practicing the method in accordance with the present invention. A therapeutic ORC formulation made in accordance with Example 6 modified to produce an ORC having approximately 99% $MgO_2$ and 1% surfactant, identified below as "0-1." A second ORC formulation was prepared in accordance with Example 5, modified by the use of Na istheionate as the surfactant, to produce an ORC having approximately 96% $MgO_2$, 3% phosphate and 1% surfactant, identified below as "3-1." The formulations were applied to each of the test zones for a total test period of 12 weeks as follows:

| Test Zone | Dosage | Frequency |
|---|---|---|
| 1 | ½ pound 0-1 per 1000 square feet | Once every 2 weeks |
| 2 | 1 pound 0-1 per 1000 square feet | Once every 2 weeks |
| 3 | 2 pounds 0-1 per 1000 square feet | Once every 2 weeks |
| 4 | ½ pound 3-1 per 1000 square feet | Once every 2 weeks |
| 5 | 1 pound 3-1 per 1000 square feet | Once every 2 weeks |
| 6 | 2 pounds 3-1 per 1000 square feet | Once every 2 weeks |

EXAMPLE 11

A series of greens having Bermuda grass turf at a golf course in Florida were diagnosed as affected by black layer. Diagnosis was accomplished as recited in Example 10.

A series of sections of the affected turf were utilized to demonstrate the efficacy and dose dependency relationship in practicing the method in accordance with the present invention. Two therapeutic ORC formulations were made as described in Example 10, and applied to each of the test zones over a total test period of 12 weeks as follows:

| Test Zone | Dosage | Frequency |
|---|---|---|
| 1a | 2 pounds 3-1 per 1000 square feet | Once every 2 weeks |
| 1b | 4 pounds 3-1 per 1000 square feet | Once every 2 weeks |
| 1c | 8 pounds 3-1 per 1000 square feet | Once every 2 weeks |
| 2a | 2 pounds 0-1 per 1000 square feet | Once every 2 weeks |
| 2b | 4 pounds 0-1 per 1000 square feet | Once every 2 weeks |
| 2c | 8 pounds 0-1 per 1000 square feet | Once every 2 weeks |
| 3 | 4 pounds 0-1 per 1000 square feet | Once every 2 weeks |
| 4 | 4 pounds 3-1 per 1000 square feet | Once every 2 weeks |

EXAMPLE 12

A series of greens having Bermuda grass turf at a golf course in Florida was diagnosed as affected by black layer. Diagnosis was accomplished as described in Example 10.

A series of sections of the affected turf were utilized to demonstrate the dose dependency in practicing the method in accordance with the present invention. A therapeutic formulation made as described in Example 10 was applied to each of the test zones over a total test period of 12 weeks as follows:

| Test Zone | Dosage | Frequency |
|---|---|---|
| 1a | 1 pound 3-1 per 1000 square feet | Once every 2 weeks |
| 1b | 2 pounds 3-1 per 1000 square feet | Once every 2 weeks |
| 1c | 4 pounds 3-1 per 1000 square feet | Once every 2 weeks |
| 2a | 1 pound 3-1 per 1000 square feet | Once every 2 weeks |
| 2b | 2 pound 3-1 per 1000 square feet | Once every 2 weeks |
| 2c | 4 pound 3-1 per 1000 square feet | Once every 2 weeks |
| 3a | 1 pound 0-1 per 1000 square feet | Once every 2 weeks |
| 3b | 2 pounds 0-1 per 1000 square feet | Once every 2 weeks |
| 3c | 4 pounds 0-1 per 1000 square feet | Once every 2 weeks |

RESULTS

The results were evaluated commencing two weeks following initial application (immediately prior to second application) and at four weeks following initial application. As compared to control areas, up to a 90% reduction in black layer was achieved following four weeks from initial application, with direct correlation to temperature, humidity, irrigation, rainfall, condition severity, dose amount and number of applications. Black layer began to reappear four to six weeks after suspension of product use, again on a dose specific basis. Heavier dosages during the initial applications resulted in a longer residual black layer control. Surface algae were controlled in the same manner.

The visual observations of the test zones after two weeks were slight reduction in odor in black layer, slight reduction in percolation rate, slight softening of thatch layer and greening of top growth in area under stress.

Following the foregoing observations, the ORC was applied again. A second set of visual observations were made after four weeks with the following results:

Further reduction in odor in black layer
Increase in percolation rate
Reduction in oversaturation of water
Reduction in surface algae
Continued softening of thatch
Continued greening of top growth in stress area
Reduced visible black layer
Roots starting to penetrate black layer
Increased root tensile strength, especially at black layer interface
Increase in fibrous root growth
Reduction in brown roots, increase in white roots
Increase in lateral top growth
Increased clippings
Top growth began filling in over and passed algae areas

EXAMPLE 13

BLACK LAYER PREVENTATIVE EFFECT

A series of greens with Bentgrass overseeded with Bermuda grass located at a golf course in Virginia which had demonstrated a propensity of black layer in summer months, was selected to demonstrate the preventative effect of methods in accordance with the present invention. Two pounds, 4 pounds and 8 pounds per 1000 square feet were added, respectively, to each of nine separate greens as follows:

| Test Zone | Dosage | Frequency |
|---|---|---|
| 1a | 2 pounds 0-1 per 1000 square feet | Once every 2 weeks |
| 1b | 4 pounds 0-1 per 1000 square feet | Once every 2 weeks |
| 1c | 8 pounds 0-1 per 1000 square feet | Once every 2 weeks |
| 2a | 2 pounds 0-1 per 1000 square feet | Once every 2 weeks |
| 2b | 4 pounds 0-1 per 1000 square feet | Once every 2 weeks |

-continued

| Test Zone | Dosage | Frequency |
|---|---|---|
| 2c | 8 pounds 0-1 per 1000 square feet | Once every 2 weeks |
| 3a | 2 pounds 0-1 per 1000 square feet | Once every 2 weeks |
| 3b | 4 pounds 0-1 per 1000 square feet | Once every 2 weeks |
| 3c | 8 pounds 0-1 per 1000 square feet | Once every 2 weeks |
| 4a | 2 pounds 0-1 per 1000 square feet | Once every 2 weeks |
| 4b | 4 pounds 0-1 per 1000 square feet | Once every 2 weeks |
| 4c | 8 pounds 0-1 per 1000 square feet | Once every 2 weeks |
| 5a | 2 pounds 3-1 per 1000 square feet | Once every 2 weeks |
| 5b | 4 pounds 3-1 per 1000 square feet | Once every 2 weeks |
| 5c | 8 pounds 3-1 per 1000 square feet | Once every 2 weeks |
| 6a | 2 pounds 3-1 per 1000 square feet | Once every 2 weeks |
| 6b | 4 pounds 3-1 per 1000 square feet | Once every 2 weeks |
| 6c | 8 pounds 3-1 per 1000 square feet | Once every 2 weeks |
| 7a | 2 pounds 3-1 per 1000 square feet | Once every 2 weeks |
| 7b | 4 pounds 3-1 per 1000 square feet | Once every 2 weeks |
| 7c | 8 pounds 3-1 per 1000 square feet | Once every 2 weeks |
| 8a | 2 pounds 3-1 per 1000 square feet | Once every 2 weeks |
| 8b | 4 pounds 3-1 per 1000 square feet | Once every 2 weeks |
| 8c | 8 pounds 3-1 per 1000 square feet | Once every 2 weeks |
| 9a | 2 pounds 3-1 per 1000 square feet | Once every 2 weeks |
| 9b | 4 pounds 3-1 per 1000 square feet | Once every 2 weeks |
| 9c | 8 pounds 3-1 per 1000 square feet | Once every 2 weeks |

The turf was visually evaluated at two weeks following initial application of ORC, with the following results:

Increase in greening of top growth in stress areas
Increased root depth and fiber
Roots white, not brown
Decrease in percolation Following the two week visual observation, the above identified dosage was repeated. At four weeks following the initial dosage, the turf was visually evaluated again with the result that no black layer had developed and an increase in percolation was observed.

In high growth seasons with no stress, there was very little difference between control and test plots. Black layer started to appear in control areas at 47 days following the initial application, with noticeable dose specific reduction in test areas. Slight increase in rooting in test areas. At 57 days from initial application, significant increase in black layer in control areas with dose specific control of black layer in test plots.

Approximately 95% of the black layer was controlled on the 8 pound per 1000 square foot test plot. Root growth was reduced in control areas, but vigorous and healthy in test plots. Root growth was approximately 2½ inches greater in depth in the 8 pound per 1000 square foot test plot as compared to the control area.

In addition to the subsoil anaerobic microorganisms discussed above, which are not directly pathogenic, several groups of anaerobic microorganisms have been identified which are directly pathogenic in plants and animals. These organisms thrive in the absence of oxygen. The release of oxygen into their environment, is therefore a practical method of control.

The role of oxygen in the expression of virulence by pathogens involves complex biochemistry. In general, the concept or virulence translates, at the molecular level, to the production of enzymes which enable certain organisms to become pathogens. The amount of oxygen in the environment regulates the production of those key enzymes.

Using the example of *Erwinia carotovora*, the causal organisms in various soft-rot diseases, digestive enzymes are produced which macerate plant tissues. The expression of these enzymes defines virulence and without them the pathogen is disarmed. Enzyme production is part of a genetic mechanism that is induced and maintained by a lack of oxygen in the environment.

However, the control of pathogen production is only one of oxygen's roles. There are several defensive biochemical systems, that help plants resist pathogens, which are induced and maintained by oxygen. These host defense mechanisms are also adversely affected by anaerobic stress. Typical examples are the oxygen dependent maintenance of certain enzymes such as hydroxymethyl gluteral Co A reductase and phenylalanine ammonia lyase.

It has been determined by the inventors herein that supplementary oxygen, as deliverable by ORC formulations in accordance with the present invention, can control the growth and virulence of certain pathogens. Similarly, ORCs can be critical in the maintenance of key biochemical mechanisms in the past, implicated in the maintenance of disease resistance.

Thus, in accordance with a further aspect of the present invention, there is provided a method of applying an effective amount of an ORC of the type disclosed herein to control obligate anaerobes via the oxygen release mechanism; oxygen being toxic to these organisms. In the case of facultative anaerobes, which can tolerate or stay virulent at relatively low levels of oxygen, control would be achieved with higher dosages, as will be apparent to one of skill in the art based upon the disclosure herein. Properly sized, time release and surfactant amended metal peroxides, with or without additional additives, would have all of the advantages previously discussed, relative to these applications.

Two important specific applications for anaerobic disease control are in the areas of post harvest physiology, and as a pre-planting treatment. Post harvest physiology is a branch of agricultural science that concerns itself with preservation of the harvest. Certain major commodities such as potatoes are susceptible to soft rot during storage. The causal organism is *Erwinia carotovora* discussed previously. When a potato becomes wet, the layer of water, in particular the water that can infiltrate a wound, can become anaerobic. In this instance, *E. carotovora* can become "armed and dangerous," genetically speaking. This scenario also applies to any other anaerobic organisms and their potential impact on other susceptible crops.

ORC, utilized in the following Experiment, is unstable above about 160° C. and releases oxygen when wet. 1 gram of material holds 0.14 grams of oxygen (14% available oxygen). This material is prepared by reacting 100 g MgO with sufficient $H_2O_2$ to produce 48.95 g $MgO_2$ and 51.05 g of MgO.

EXAMPLE 14

*E. CAROTOVORA* GROWTH IN THE PRESENCE OF ORC

To determine if *E. Carotovora* ("Ecc") grows in the presence of ORC, the compound was added to cooled, molten agar (55° C.; 1.5% Difco bacteriological agar in water) in the bottom of 90 cm petri dishes. The specific ORC utilized herein is 14% available oxygen $MgO_2$. PEM (0.1% polygalacturonic acid, 0.5% tryptone, and 0.5% yeast extract; pH 7.0) was inoculated with an overnight static culture of Ecc in LB (Miller, 1972) to a turbidity of <0.00 at 600 nm ($\leq 10^6$ cfu/ml) and dispensed in 10 ml portions into the petri dishes on top of the hardened agar containing ORC. Some dishes were incubated aerobically with gyratory agitation (50 rpm) and some were incubated statically with $CO_2/H_2$ generators in anaerobic jars (BBL GasPac System, Becton Dickinson and Co., Cockeysville, Md.) (Mahre & Kelman, 1983). All dishes were incubated at 24°±2° C. for 132 hr. The PEM cultures were harvested by pipetting and the turbidity measured at 600 nm.

TABLE 1

Effect of the Oxygen-Releasing Compound (ORC) on the Turbidity of *Erwinia carotovora* subsp. *carotovora* (Ecc) Cultured In Protein Extraction Medium (PEM)

| Percent ORC (w/v) | Turbidity at 660 nm for Cells Cultured Anaerobically |
|---|---|
| None | 0.12/0.10[a] |
| 0.01 | 0.22 |
| 0.10 | <0.00 |
| 1.00 | <0.00 |

[a]For the second measurement, a plate containing agar but no ORC was incubated separately in an anaerobic jar to determine if turbidity on a similar plate incubated with the ORC-containing plates was affected by ORC in the other plates.
[b]NT. = not tested.

RESULTS

ORC affects the growth of Ecc in a positive manner at low concentration (0.01%) in anaerobic conditions (Table 2). At the higher concentrations tested, ORC was inhibitory. Aerobically, growth was not adversely affected in a significant manner at 0.01%, but growth was severely affected at higher concentrations of ORC tested.

EXAMPLE 15

INHIBITION OF POTATO SOFT ROT

A series of 100 g slices of potato were prepared and inoculated with *Erwinia carotovora*. Half of the group were then dusted with the powder form of the ORC utilized in Example I above. The results were dramatic. After one week an average of 14.93 grams of tissue had rotted in the control as compared to 0.83 grams among the treated pieces.

Quite surprisingly, application of ORC was also found to stimulate sprouting in the treated potato sections. Thus, the dusting of propagation potato pieces with an effective concentration of ORC will achieve the dual benefit of disease control and enhanced sprouting.

In summary, the evidence shows that ORC suppresses growth of Ecc, see Table 1, and releases $O_2$ in cultures. With respect to the treatment of plant material, ORC demonstrated both the ability to substantially prevent post harvest soft rot in potatoes, via the controls of Ecc and support of host defense mechanisms, and the ability to enhance sprouting when utilized as a pre-planting treatment of potato sections.

EXAMPLE 16

POST HARVEST STORAGE OF CALLA LILY RHIZOMES

Calla lilies are produced from rhizomes (fleshy storage roots). When these rhizomes are planted, they sprout and produce the saleable crop.

A mature plant can be dug up to collect rhizomes which are often stored for future planting. *Erwinia carotovora* can devastate the stored rhizomes as well as planted rhizomes or whole plants.

In this experiment, about 56 rhizomes were placed into storage. Half were dusted with $MgO_2$ (20% activity). The other half were not dusted. After approximately two months, the weight differences were gathered as an indicator of erwinia mediated disease. The results are depicted in FIG. 1, which demonstrates a significant storage improvement in the treated rhizomes.

EXAMPLE 17

PHYTHIUM CONTROL

Pure $MgO_2$ with an activity of 20% was mixed with corn meal agar when medium had cooled to <50° F. Four replicates were done on each species.

Petri dishes were inoculated with plugs of the phythium fungi. The experiments began with a 5 mm diameter plug. Effects on growth are then a function of the increase in diameter of this plug (colony size in mm).

Figure 2:
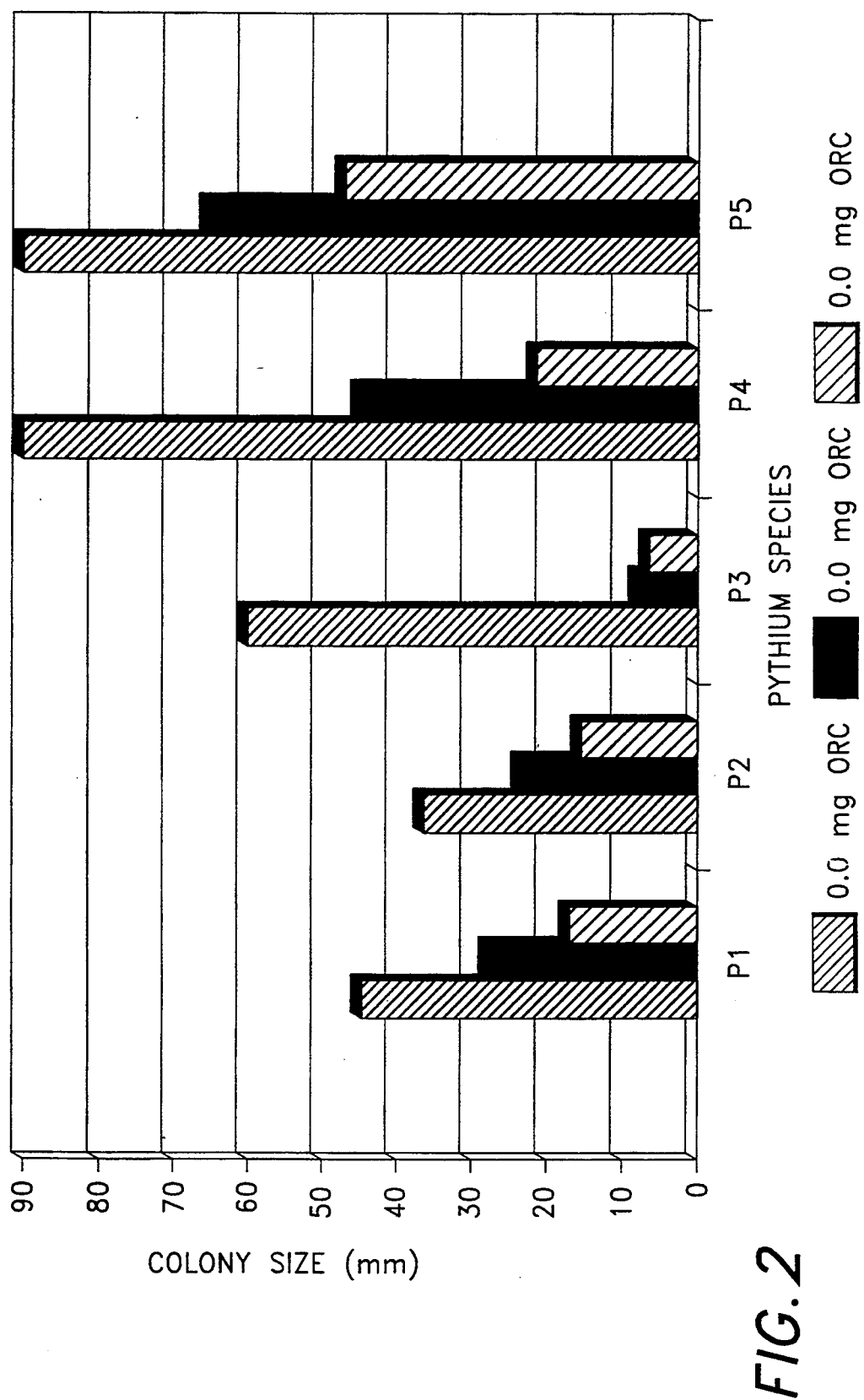
FIG. 2 illustrates the dose response of five species of phythium as a result of treatment in accordance with the present invention.
Figure 3:
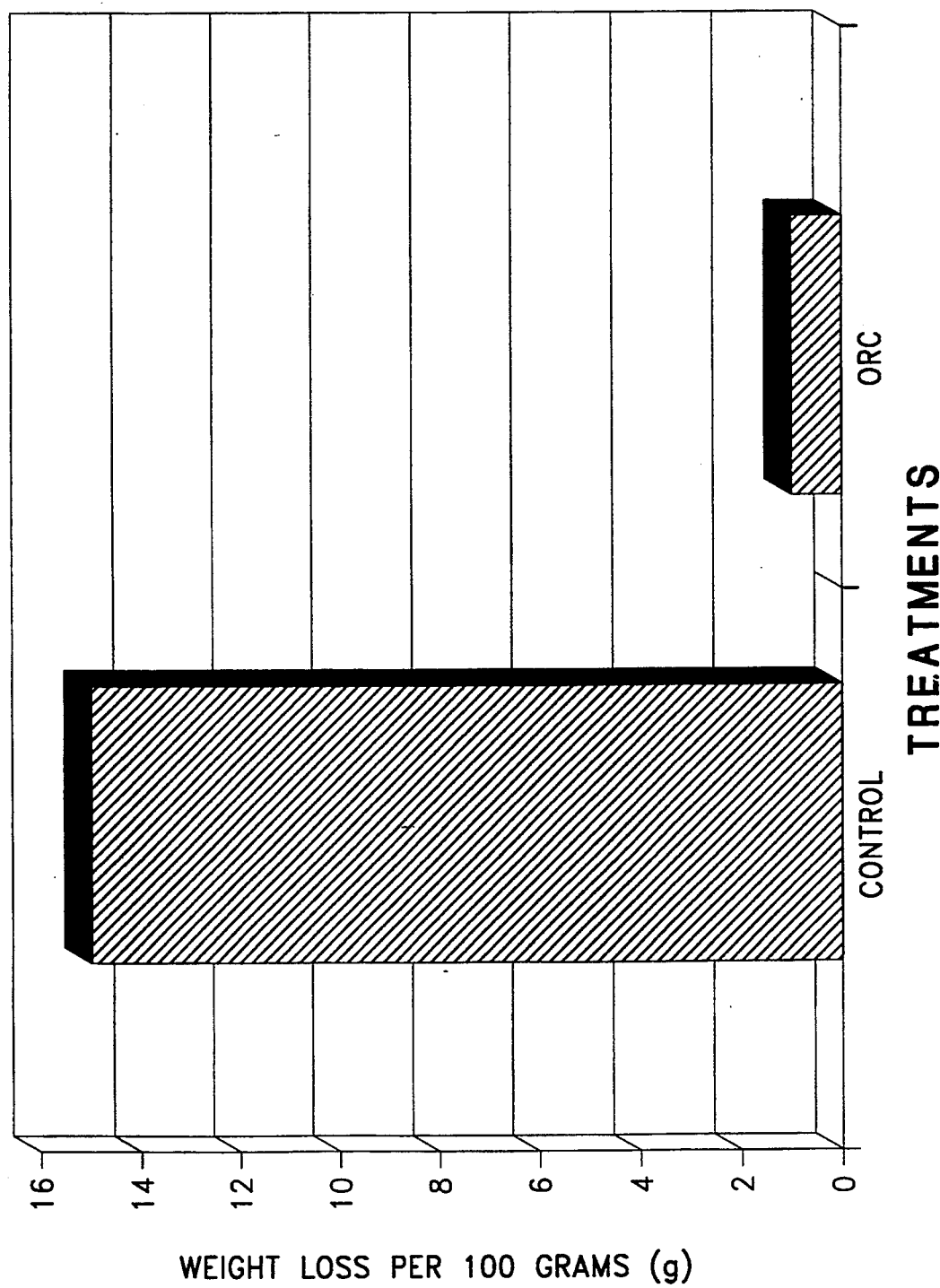
FIG. 3 illustrates the effect of ORC treatment at the pre-use, pre-shipment, pre-storage or pre-planting stage on potato sections in accordance with the present invention.

The control was 0.0 mg ORC and tests were conducted at 2 levels, 0.5 and 1.0 mg ORC per dish. Petri dishes typically hold 20–25 ml of media, therefore, using 25 ml, we have 0.5 mg/25 ml or 20 ppm and 1 mg/25 ml or 40 ppm of ORC in the system. At 20% $O_2$ these figures would be 4 ppm and 8 ppm of oxygen respectively; which incidentally is being liberated over approximately 4 days by first order kinetics. The results are depicted in FIG. 2, which demonstrates a beneficial dose response for treatment of the following five species of phythium: *Phythium torulosum, P. vanterpoolii, P. graminicola, P. ultimum* and *P. aphanidermatum*.

Based on the foregoing, a wide range of applications of the method of the present invention are contemplated by the inventors, at the post harvest storage, pre-planting, preventative and therapeutic stages. Plant organs for consumption which may or may not be capable of utility in propagation, preferentially asexual propagation, or for direct consumption or reuse, such as tubers, rhizomes, bulbs and corm are all potentially beneficially treated.

The above description discloses the best mode contemplated of carrying out the present invention. This invention is, however, susceptible to modifications of the formulations discussed above. Consequently, it is not the intention to limit this invention to the particular embodiments disclosed. On the contrary, the intention is to cover all modifications and alternatives coming within the spirit and scope of the invention as generally expressed by the following claims.

We claim:

1. A method of treating media in which plants grow, said media of the type having a relatively negative reduction oxidation potential, comprising:

providing a composition comprising a metal peroxide intercalated with a source of simple phosphate ion, said source of simple phosphate ion being a salt of phosphorus in which for each phosphorus containing salt, the negatively charged portion of the compound contains only one atom of phosphorus, said composition being prepared by a method comprising:

reacting a metal oxide, metal hydroxide, or metal carbonate with an aqueous solution of hydrogen peroxide in the presence of said source of simple phosphate ion; and thereafter drying the product produced in the reacting step to remove the water therefrom and to provide an intercalated composition;

said method of treating media further comprising applying said intercalated composition to the media in an amount effective to cause said intercalated composition to consistently release to the media an effective amount of oxygen, said oxygen providing an increase in the reduction oxidation potential over a time period greater than 100 hours that offsets the negative effects of having a relatively negative reduction oxidation potential, thereby enhancing plant growth and appearance.

2. The method of claim 1, wherein the media has an absolute negative reduction oxidation potential and wherein a sufficient amount of said intercalated composition is applied to the media to change the reduction oxidation potential of the media from absolute negative to absolute positive.

3. The method of claim 1, wherein the peroxide is selected from the group consisting of calcium peroxide, potassium metal peroxide and magnesium peroxide.

4. The method of claim 3, further comprising adding a surfactant in an amount which is substantially non-toxic to plants to the intercalated composition before the applying step.

5. The method of claim 4, wherein the surfactant is added in an amount from 0.03 to 1.60 grams of surfactant per gram of metal peroxide.

6. The method of claim 1, wherein the source of simple phosphate ion is selected from the group consisting of potassium dihydrogen phosphate, dipotassium hydrogen phosphate, urea phosphate, monoammonium phosphate, diammonium phosphate and mixtures thereof.

7. The method of claim 6, wherein the source of simple phosphate ion is present in the amount of from about 0.03 to about 1.60 grams of compound per gram of peroxide.

8. The method of claim 1, wherein said media comprises a soil area that has a propensity to develop undesirable levels of anaerobic microorganism activity.

9. A method of treating media in which plants grow, comprising:
providing a composition comprising magnesium peroxide intercalated with a source of simple phosphate ion, said composition being prepared by a method comprising:
reacting magnesium oxide, magnesium hydroxide, or magnesium carbonate with an aqueous solution of hydrogen peroxide in the presence of said source of simple phosphate ion; and thereafter
drying the product produced in the reacting step to remove the water therefrom and to provide an intercalated composition;
applying said intercalated composition to the media in an amount effective to cause said intercalated composition to produce a consistent increase in the reduction oxidation potential of the media for a time period of greater than 100 hours, thereby enhancing plant growth and appearance.

10. The method of claim 9, wherein the source of simple phosphate ion is selected from the group consisting of potassium dihydrogen phosphate, dipotassium hydrogen phosphate, urea phosphate, monoammonium phosphate, diammonium phosphate and mixtures thereof.

11. The method of claim 9, wherein the source of simple phosphate ion is added in an amount from 0.03 to 0.80 grams of phosphate ion per gram of magnesium peroxide.

12. The method of claim 9, further comprising adding a surfactant in an amount which is substantially non-toxic to plants to the intercalated composition before the applying step.

13. The method of claim 12, wherein the surfactant is added in an amount of from about 0.005 to 0.0 10 grams of surfactant per gram of magnesium peroxide.

14. The method of claim 12, wherein the surfactant is selected from the group consisting of:
(a) long chain alcohol ethoxylate sulfates of the formula $RO-(CH_2CH_2O)-_n SO_3Na$ where R is about $C_{12}$ to $C_{18}$, and n is no greater than about 9 to 10;
(b) long chain acyl taurides of the formula $RCON(CH_3)C_2H_4SO_3Na$ where R is about $C_{14}$ to $C_{20}$; and
(c) long chain ethoxylated alcohols of the formula $RO-(CH_2CH_2O)-_n H$ where R is about $C_{14}$ to $C_{20}$, and n is no greater than about 9 to 10.

15. A method of treating an undesirable soil condition of the type associated with anaerobic microorganism activity, comprising the steps of:
identifying a soil area which exhibits indicia of undesirable levels of anaerobic microorganism activity; and
administering to the identified soil area an effective amount of a composition comprising a metal peroxide intercalated with a buffer system, said buffer system comprising a source of simple phosphate ion, wherein said source of simple phosphate ion comprises at least one of potassium dihydrogen phosphate or dipotassium hydrogen phosphate, wherein said composition is prepared by a method comprising:
reacting a metal oxide, metal hydroxide, or metal carbonate with an aqueous solution of hydrogen peroxide in the presence of said source of simple phosphate ion; and thereafter
drying the product produced in the reacting step to remove the water therefrom and to provide an intercalated composition.

16. A method as in claim 15, wherein said administering step is accomplished by applying said composition in aqueous slurry form.

17. The method of claim 15, wherein said buffer system comprises both potassium dihydrogen phosphate and dipotassium hydrogen phosphate.

18. The method of claim 17, wherein said metal peroxide is selected from the group consisting of magnesium peroxide, calcium peroxide, potassium peroxide and mixtures thereof.

19. A method of treating an undesirable soil condition of the type associated with anaerobic microorganism activity, comprising the steps of:
identifying a soil area which exhibits indicia of undesirable levels of anaerobic microorganism activity; and
administering to the identified soil area an effective amount of a composition comprising a metal peroxide intercalated with a source of simple phosphate ion, wherein said composition is prepared by the method comprising:
reacting a metal oxide, metal hydroxide, or metal carbonate with an aqueous solution of hydrogen peroxide in the presence of said source of simple phosphate ion; and thereafter
drying the product produced in the reacting step to remove tile water therefrom and to provide an intercalated composition.

20. The method of claim 19, wherein said metal peroxide consists essentially of magnesium peroxide.

* * * * *

UNITED STATES PATENT AND TRADEMARK OFFICE
CERTIFICATE OF CORRECTION

PATENT NO. : 5,395,419
DATED      : March 7, 1995
INVENTOR(S): William A. Farone, et al It is certified that error appears in the above-indentified patent and that said Letters Patent is hereby corrected as shown below:

In the figure appearing on the Abstract and in Fig. 2, in the second occurrence of "0.0" with --0.5-- and the third occurrence of "0.0" with --1.0--.

Signed and Sealed this

Twelfth Day of December, 1995

Attest:

BRUCE LEHMAN

*Attesting Officer*    *Commissioner of Patents and Trademarks*